(12) United States Patent
Shiokawa et al.

(10) Patent No.: US 7,126,030 B2
(45) Date of Patent: Oct. 24, 2006

(54) STABILIZED HYDROXYPIVALALDEHYDE

(75) Inventors: Yoshihiro Shiokawa, Chiba (JP);
Hiroaki Shigeta, Okayama (JP);
Ikutaro Kuzuhara, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 11/063,606

(22) Filed: Feb. 24, 2005

(65) Prior Publication Data

US 2005/0192466 A1    Sep. 1, 2005

(30) Foreign Application Priority Data

Feb. 25, 2004    (JP) ............................ 2004-049048

(51) Int. Cl.
*C07C 45/00*    (2006.01)
*C07C 47/00*    (2006.01)
(52) U.S. Cl. ..................................... 568/492; 568/496
(58) Field of Classification Search .................... None
See application file for complete search history.

(56) References Cited

U.S. PATENT DOCUMENTS 4,036,888 A * 7/1977 Couderc et al. ............ 568/464

FOREIGN PATENT DOCUMENTS

DE    25 47 540 A1    5/1976
JP    61-18741    1/1986

OTHER PUBLICATIONS

European Search Report, dated Jun. 21, 2005, for Application No. 05100958.7-2103.

* cited by examiner

*Primary Examiner*—Sikarl A. Witherspoon
(74) *Attorney, Agent, or Firm*—Antonelli, Terry, Stout and Kraus, LLP.

(57) ABSTRACT

In the method of the invention, hydroxypivalaldehyde (3-hydroxy-2,2-dimethylpropanal) and/or its dimer is stored under solid conditions containing an amount of water. By storing such solid conditions, hydroxypivalaldehyde and/or its dimer is stored for a long period of time without reducing its purity.

11 Claims, No Drawings

STABILIZED HYDROXYPIVALALDEHYDE

BACKGROUND OF THE INVENTION

1. Field of the Invention

The present invention relates to a stabilized hydroxypivalaldehyde (3-hydroxy-2,2-dimethylpropanal, hereinafter referred to as HPA) and a method of stably storing HPA.

2. Description of the Prior Art

HPA is generally produced by aldol condensation of isobutylaldehyde (hereinafter referred to as IBAL) and formaldehyde or a formaldehyde aqueous solution (formalin) in the presence of a basic catalyst such as amines. Although the aldol condensation generally proceeds under either acidic or basic conditions, the synthesis of HPA is generally conducted under basic conditions in the presence of a basic catalyst, because HPA has both a carbonyl group and a hydroxyl group and so easily undergoes self-condensation by acetalization under acidic conditions. After the reaction, the low-boiling components such as unreacted IBAL and formaldehyde are removed by distillation to obtain a reaction production liquid. HPA is generally used as a synthetic intermediate. If neopentyl glycol (hereinafter referred to as NPG), 3-hydroxy-2,2-dimethyl monohydroxypivalate (ester glycol, hereinafter referred to as ESG), etc., which are by-produced during the synthesis of HPA, are intended as the final products, the reaction product liquid of HPA is immediately used in a crude form in the subsequent steps without further purification.

As a method for producing pure HPA, there has been disclosed a method in which a purified HPA is produce by subjecting IBAL and formaldehyde or formalin to aldol condensation in the presence of an amine catalyst to produce HPA, removing low-boiling components by distillation to obtain crude HPA, and purifying the crude HPA by addition of water, crystallization of HPA under cooling, solid-liquid separation of HPA, and washing with water (U.S. Pat. No. 4,036,888 and JP 6-29206B). It has been reported that HPA exists in equilibrium between monomer and dimer (Journal of the Chemical Society, Perkin Transactions II, vol. 3, p. 189–192, 1978) as illustrated below,

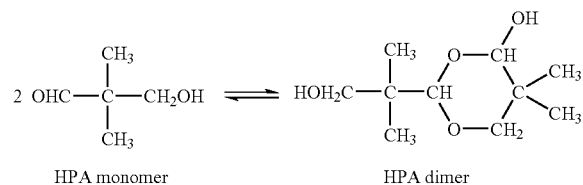

HPA monomer    HPA dimer and the purified HPA is usually obtained in the form of a dimer. Is has been also disclosed that the HPA dimer show a reactivity equivalent to that of the HPA monomer (JP 1-299239A and JP 5-117187A).

If the crude HPA after removing low-boiling components by distillation is stored under solution conditions containing a basic catalyst, etc., the amount of by-products increases within a short period of time after the distillation to unfavorably reduce the concentration of HPA and/or its dimer. If HPA and/or its dimer is purified by crystallization as proposed in JP 6-29206B, etc., a large amount of HPA and/or its dimer is left in the mother liquor to significantly reduce the yield, this requiring an additional step for recovering HPA and/or its dimer from the mother liquor. Since the wet cake of HPA and/or its dimer is poor in storage stability, the purity can be maintained only in an extremely short period of time. If NPG, ESG, etc. are not the final target compounds and HPA and/or its dimer is not intended to be immediately used as the synthetic intermediate(s), the storage of HPA and/or its dimer which is produced in advance of the use or the transportation for its use at a distant place are extremely limited.

To prevent the purity of HPA and/or its dimer from being lowered, the wet cake obtained in the crystallizing operation for purification should be dried. When heated to 55° C. or higher for drying, HPA and/or its dimer is melted at the initial stage of drying where the water content is still high to increase the escaped amount thereof as the drying proceeds. Simultaneously, as illustrated below, two molecules of HPA react to form ESG by Tishchenko reaction.

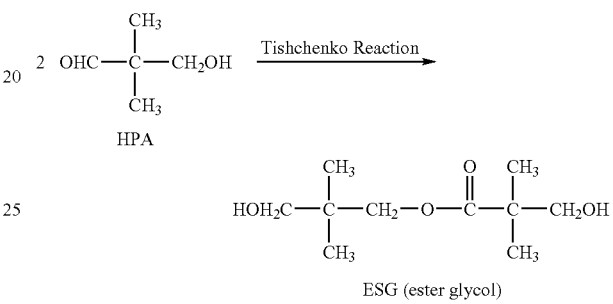

ESG (ester glycol)

To avoid these problems, the drying of the wet cake is effected generally by vacuum dry at temperatures less than 55° C. without heating to high temperatures. However, HPA is lost by sublimation under reduced pressure conditions because of its high vapor pressure and the sublimated HPA causes other problems such as clogging of vacuum lines. Therefore, the wet cake is dried by heating at temperatures lower than 55° C. for a long period of time or dried at temperatures lower than 55° C. in a flow of dry nitrogen, etc. However, these methods make the utility consumption excessively large and are highly disadvantageous for industrial use when taking the need for apparatuses for crystallization, separation, etc. into consideration.

Since HPA is instable under solution conditions containing water or under wet cake conditions, it is generally used in subsequent step without delay after its production. As described above, although it has been proposed to dry the wet cake of HPA, the proposed method is not suitable for industrial use because of the problems mentioned above. Thus, an industrially applicable method of storing HPA for a long period of time without reducing its purity is not hitherto known in the art.

SUMMARY OF THE INVENTION

An object of the present invention is to solve the above problems about the storage stability of HPA and/or its dimer and provide a method for easily producing HPA and/or its dimer which is capable of being stably stored fro a long period of time.

As a result of extensive research in view of achieving the above object by enhancing the storage stability of HPA and/or its dimer, the inventors have found that HPA and/or its dimer containing a given amount of water completely into a solid product by cooling, irrespective of containing a large amount of water. It has been also found that such a solid product is capable of being stored stably for a long period of time even when the basic catalyst is contained, as compared with a product purified by crystallization. The invention is based on these findings.

Thus, the invention provides a solid product comprising hydroxypivalaldehyde and/or its dimer and water. The solid product may be produced by cooling a liquid containing hydroxypivalaldehyde and/or its dimer and water preferably at 50° C. or lower. The liquid to be cooled may be a reaction product solution containing hydroxypivalaldehyde and/or its dimer and water, which is obtained by subjecting isobutyl-aldehyde and formaldehyde or an aqueous solution of formaldehyde to aldol condensation in the presence of a basic catalyst and then separating low-boiling components. In a preferred embodiment, the solid product comprises 35 to 95% by weight of hydroxypivalaldehyde and/or its dimer and 5 to 65% by weight of water.

The invention further provides a method for stably storing hydroxypivalaldehyde, which comprises a step of cooling a liquid comprising hydroxypivalaldehyde and/or its dimer and water to allow the liquid to change into a solid product. The liquid preferably comprises 35 to 95% by weight of hydroxypivalaldehyde and/or its dimer and 5 to 65% by weight of water. The cooling is performed more preferably at 40° C. or lower.

DETAILED DESCRIPTION OF THE INVENTION

Formaldehyde to be used for the production of HPA and/or its dimer may be used as such or in an aqueous solution (formalin). The aldol condensation of IBAL and formaldehyde in the presence of a basic catalyst is very susceptible to the water concentration of the reaction system. If the concentration of IBAL or formaldehyde is low, the reaction rate become decreased to fail to attain a desirable yield. Therefore, the concentration of formaldehyde in formalin is preferably as high as possible. Preferred as the starting formalin is one having a formaldehyde concentration of 37% by weight or more with no or a minimized amount of methanol. A commercially available IBAL is usable in the invention while preferred is one having a content of n-butyl alcohol, etc. as low as possible and having a purity of 99% or more.

The aldol condensation for the production of HPA and/or its dimer may be performed in either batch manner or continuous manner preferably under atmospheric pressure or under pressure while shutting off the flow of air or allowing nitrogen to flow. In the batch method, IBAL, formaldehyde (formalin) and the catalyst may be supplied in any way. Aldol condensation or Cannizzaro reaction between IBAL molecules or between formaldehyde molecules may take place in some cases to reduce the yield of HPA when IBAL or formaldehyde (formalin) is brought into contact with the basic catalyst in advance. To remove this problem, it is preferred to supply the basic catalyst into a mixture of IBAL and formaldehyde (formalin). In the continuous method, like the batch method, IBAL, formaldehyde (formalin) and the catalyst may be supplied in any way. To enhance the reaction efficiency, the continuous method is preferably performed in a multi-stage manner of about 2 to 4 stages. The charge ratio of IBAL to formaldehyde is preferably 0.8 to 1.6, more preferably 0.9 to 1.4 in terms of molar equivalent. In the batch method, the reaction system is heterogeneous within several minutes after the initiation of reaction and changes into a homogeneous state with the generation of HPA. The reaction temperature is preferably 40 to 98° C., more preferably 80 to 95° C. under atmospheric pressure. In the batch method, the temperature rise stops for a time when reaching the reflux point, 62 to 65° C., of IBAL. Then, the temperature gradually rises with the generation of HPA and/or its dimer (consumption of IBAL) and is controlled finally to 80° C. or higher. The reaction is completed by keeping at 80 to 95° C. for 0.05 to 2 h. In the continuous method, the reaction proceeds in homogeneous system. The reaction temperature is preferably 50 to 98° C., more preferably 70 to 95° C., and the residence time is preferably 0.1 to 5 h, more preferably 0.3 to 3 h. The reaction temperature is controlled by heating or cooling using a jacket, coil, etc. attached to the reactor, by circulating the reaction liquid to an exterior heat exchanger for cooling, or by refluxing low-boiling components to remove heat.

Examples of the basic catalysts for use in the aldol condensation include inorganic bases such as sodium hydroxide, potassium hydroxide, sodium carbonate and potassium carbonate; and organic bases such as tertiary amines and pyridine. If the basicity is too strong, Cannizzaro reaction between HPA and/or its dimer and non-reacted formaldehyde occurs to reduce the yield of HPA and/or its dimer. If the basicity is too weak, the reaction rate becomes low. Therefore, the tertiary amine is preferably used. Examples thereof include trimethylamine, triethylamine, tripropylamine, triisopropylamine, tributylamine, triisobutylamine, N-methylpiperidine, N-ethylpiperidine, N-methylmorpholine, N-ethylmorpholine, N-methylpyrrolidine and N-ethylpyrrolidine, with trimethylamine and triethylamine being preferred because of their easy availability, and triethylamine being more preferred. The amount of the basic catalyst to be used varies depending on its kind, and preferably 0.001 to 0.5, more preferably 0.01 to 0.2 in terms of molar equivalent with respect to IBAL.

After completing the aldol condensation, a liquid comprising HPA and/or its dimer and water is obtained by distillation for removing low-boiling components mainly comprising non-reacted IBAL and formaldehyde and methanol contained in formalin as an impurity. Since the degradation of HPA and/or its dimer is accelerated with increasing temperature, the removal of low-boiling components by distillation is preferably performed under reduced pressure of about 25 to 95 kPa under which the column top temperature is allowed to become about 40 to 80° C. suitable for recovering non-reacted IBAL, etc. without problems. The distillation may be performed in either batch manner or continuous manner. To promote the removal of low-boiling components, water may be added in advance of the distillation.

The liquid comprising HPA and/or its dimer and water thus obtained is changed into a solid product by cooling. By making into the solid product, HPA and/or its dimer is stabilized against the degradation. However, if the water content is excessively high, the liquid containing HPA and/or its dimer and water is not changed into a uniform solid product, but into a liquid slurry to deteriorate the storage stability. It is disadvantageous to make the water content excessively low, because the removal of low-boiling components should be performed at high temperatures for a long period of time, increasing the amount of HPA and/or its dimer which is degraded during the removal of low-boiling components. Considering the above, preferred is a liquid comprising 35 to 95% by weight of HPA and/or its dimer and 5 to 65% by weight of water, and more preferred is a liquid comprising 60 to 90% by weight of HPA and/or its dimer and 10 to 40% by weight of water.

The liquid comprising HPA and/or its dimer and water is cooled at 50° C. or lower, preferably 40° C. or lower. At temperatures higher than 50° C., the change of the liquid into the solid product is extremely slow to increase the amount of HPA and/or its dimer degraded before the change into the solid product is completed. The lower limit of the cooling temperature is not particularly specified and a temperature about 10 to 50° C. is practically sufficient for cooling because no additional equipment is required. The temperature of HPA and/or its dimer is lowered to the cooling temperature (10 to 50° C.) preferably within 50 h after its production, more preferably within 10 h after its production, and still more preferably as promptly as possible after its production. If it takes a long period of time until the temperature is lowered to the cooling temperature, the HPA and/or its dimer is inevitably held at temperatures higher than the cooling temperature to increase the amount of degradation. The cooling time after the cooling is started until the change into the solid product is completed is not critical, and preferably one hour or longer, preferably 10 h or longer. If shorter than one hour, the change into the solid product is not completed to leave a liquid portion, making the handling thereof difficult. The cooling operation is finished after confirming the completion of the change into the solid product. To allow the liquid to uniformly change into the solid product, the container containing the liquid comprising HPA and/or its dimer and water may be stirred or shaken. The solid product is stored at temperatures at which the solid state is maintained, preferably at 10 to 40° C.

If the liquid comprising HPA and/or its dimer and water is cooled and changed into the solid product in a sealed can container, the solid product firmly adheres to the inner wall of the sealed can container to make it difficult to take out the solid product without destroying the can container. If re-melting under heating for taking out, the melted HPA and/or its dimer is rapidly degraded. Alternatively, the liquid may be cooled and changed into the solid product in a vat, etc. and then crashed into pieces for easy handling. However, this method is not suitable for the treatment of a large amount. Therefore, the liquid comprising HPA and/or its dimer and water is cooled and changed into the solid product preferably in a resin-made bag container. By changing into the solid product in an inexpensive sealable bag, for example, a bag container made of a resin such as polyethylene, the storage and transportation of the solid product comprising HPA and/or its dimer and water become easy. The solid product is taken out of the container for use only by breaking the container. After changing the liquid comprising HPA and/or its dimer and water into the solid product in a resin-made bag container, etc., the solid product may be crashed into pieces so as to allow the reaction using HPA and/or its dimer as the starting material to proceed easily.

The invention is described in more detail with reference to the examples. However, it should be noted that the following examples are not intended to limit the scope of the invention thereto. In the following, "%" and "part(s)" are based on weight unless otherwise noted.

The gas chromatographic analysis of the solid comprising HPA and/or its dimer and water was made on an acetone solution of the solid product. HPA and/or its dimer is observed as HPA.

SYNTHESIS EXAMPLE 1

Synthesis of HPA and/or its Dimer

Into 595 parts of IBAL and 657 parts of a 37% formalin charged into a reactor, 33 parts of triethylamine (hereinafter referred to as TEA) was added over 5 min at 40° C. under stirring in a flow of nitrogen. The reaction was initiated at the same time when the addition of TEA was begun, and the temperature of the reaction liquid reached 65° C. at the completion of the addition of TEA. Thereafter, the reaction temperature was gradually raised by suitably continuing the heating and reached 90° C. after 30 min. After continuing the reaction for additional 5 min at 90° C., the reaction was stopped by externally cooling the reaction liquid to 60° C. Then, low-boiling components such as unreacted IBAL, TEA and methanol were removed by distillation at 60 to 70° C. under 53 kPa to obtain a reaction product liquid (hereinafter referred to as crude HPA), which was then analyzed by gas chromatography (hereinafter referred to as GC) for the chemical composition. The results are shown in Table 1.

EXAMPLE 1

A 18-L polyethylene container with a screw cap ("Baron Box" of grade 18A available from The Koizumi Jute Mills Ltd.) was filled up with the solution of crude HPA obtained in Synthetic Example 1 at 60° C., and then hermetically sealed. Upon cooling at 20° C. for 48 h, the solution completely changed to a solid product. After maintaining the temperature at 20° C. for three weeks or three months, the solid product was analyzed by GC for the chemical composition. The results are shown in Table 1.

EXAMPLE 2

A 200-L polyethylene container with a screw cap ("Fuji Liner 200", back-in-box available from Fujimori Kogyo Co., Ltd.) was filled up with the solution of crude HPA obtained in Synthetic Example 1 at 60° C., and then hermetically sealed. Upon cooling at 20° C. for 48 h, the solution completely changed to a solid product. After maintaining the temperature at 20° C. for three weeks or three months, the solid product was analyzed by GC for the chemical composition. The results are shown in Table 1.

COMPARATIVE EXAMPLE 1

The solution of crude HPA obtained in Synthetic Example 1 was stored in a sealed container under a solution condition at 60° C. After one weak, the solution was analyzed by GC for the chemical composition. The results are shown in Table 1.

TABLE 1

| | Chemical Composition (percent by weight) | | | | | | | |
|---|---|---|---|---|---|---|---|---|
| | HPA | IBAL | FAL | TEA | NPG | ESG | BNE | Water |
| Synthesis Example 1 | 62.4 | 0.3 | 2.4 | 0.3 | 0.6 | 2.0 | 0.2 | 28.5 |
| Example 1 | | | | | | | | |
| after 3 weeks | 62.2 | 0.3 | 2.3 | 0.3 | 0.7 | 2.1 | 0.2 | 28.5 |
| after 3 months | 62.1 | 0.3 | 2.2 | 0.3 | 0.7 | 3.0 | 0.2 | 28.6 |
| Example 2 | | | | | | | | |
| after 3 weeks | 62.0 | 0.3 | 2.3 | 0.3 | 0.7 | 2.5 | 0.2 | 28.6 |
| after 3 months | 61.8 | 0.3 | 2.1 | 0.3 | 0.7 | 3.0 | 0.2 | 28.8 |

TABLE 1-continued

| | Chemical Composition (percent by weight) | | | | | | |
|---|---|---|---|---|---|---|---|
| | HPA | IBAL | FAL | TEA | NPG | ESG | BNE | Water |
| Comparative Example 1 | | | | | | | | |
| after one week | 56.2 | 0.2 | 1.8 | 0.3 | 0.8 | 8.0 | 0.3 | 28.7 |

HPA: hydroxypivalaldehyde
IBAL: isobutylaldehyde
FAL: formaldehyde
TEA: triethylamine
NPG: neopentyl glycol
ESG: 3-hydroxy-2,2-dimethyl monohydroxypivalate
BNE: neopentyl glycol monoisobutyrate

COMPARATIVE EXAMPLE 2

A crude HPA (100 parts by weight) was added with 278 parts by weight of water so as to adjust the concentration of HPA and/or its dimer to 16.5%. After cooling to 35° C., the mixture was stored under stirring for one hour and then subjected to a solid-liquid separation using a top-discharging centrifugal separator. By the separating operation, 315.6 parts by weight of mother liquor was discharged and 62.4 parts by weight of HPA cake was obtained. The HPA cake was washed with 125 parts by weight of pure water. By the washing operation, 127.6 parts by weight of washings was discharged and 60 parts by weight of washed wet HPA was obtained. The chemical composition of the washed wet HPA determined by GC analysis was 61.4% of HPA and/or its dimer and 38.6% of water, and other components were not detected. After storing the washed wet HPA at 20° C. for three weeks, the chemical composition thereof determined by GC analysis was 58.3% of HPA and/or its dimer, 2.0% of ESG and 38.7% of water.

HPA has a hydroxyl group and a carbonyl group in its molecule and is useful as a raw material for the production of neopentyl glycol, calcium pantothenate, spiroglycol, hydroxypivalic acid and its esters, pivalolactone, etc. In the method of the invention, IBAL and formaldehyde or an aqueous solution of formaldehyde are subjected to aldol condensation in the presence of a basic catalyst. After removing low-boiling components by distillation, the reaction product solution containing a given amount of water is cooled to change it completely into a solid product. By storing under such a solid condition, HPA and/or its dimer is stored for a long period of time without reducing the purity although it is easily degraded under a solution condition containing the basic catalyst or under a wet cake condition. By the method of the invention, the use of HPA and/or its dimer after storage or transportation is made easy. Thus, the present invention is of great value.

What is claimed is:

1. A uniform solid product comprising 35 to 95% by weight hydroxypivalaldehyde and/or its dimer and 5 to 65% by weight of water, which is produced by cooling an aqueous liquid containing hydroxypivalaldehyde and/or its dimer, thereby completely changing the aqueous liquid into the uniform solid product.

2. The uniform solid product according to claim 1, wherein the aqueous liquid is a reaction product solution obtained by subjecting isobutylaldehyde and formaldehyde or an aqueous solution of formaldehyde to aldol condensation in the presence of a basic catalyst and then separating low-boiling components by distillation.

3. The uniform solid product according to claim 1, wherein the cooling is performed at 50° C. or lower.

4. A method for storing hydroxypivalaldehyde, which comprises a step of cooling an aqueous liquid containing hydroxypivalaldehyde and/or its dimer, thereby completely changing the aqueous liquid into a uniform solid product comprising 35 to 95% by weight of hydroxypivalaldehyde and/or its dimer and 5 to 65% by weight of water.

5. The method according to claim 4, wherein the aqueous liquid contains 35 to 95% by weight of hydroxypivalaldehyde and/or its dimer and 5 to 65% by weight of water.

6. The method according to claim 4, wherein the cooling is performed at 50° C. or lower.

7. The method according to claim 4, wherein the cooling is performed in a container made of resin.

8. The uniform solid product according to claim 1, wherein the cooling is performed at 40° C. or lower.

9. The method according to claim 5, wherein the liquid contains 60 to 90% by weight of hydroxypivalaldehyde and/or its dimer and 10 to 40% by weight of water.

10. The method according to claim 6, wherein the cooling is performed at 40° C. or lower.

11. The method according to claim 4, wherein during said step of cooling, the aqueous liquid is stirred or shaken.

* * * * *